United States Patent [19]

Balke et al.

[11] 4,012,506
[45] Mar. 15, 1977

[54] PYRIMIDYL THIO- AND DITHIO-PHOSPHORIC ACID ESTERS

[75] Inventors: David E. Balke, Mobile, Ala.; Ward H. Oliver, La Place, La.

[73] Assignee: Ciba-Geigy Corporation, Ardsley, N.Y.

[22] Filed: July 3, 1975

[21] Appl. No.: 593,144

[52] U.S. Cl. .......................... 424/200; 260/251 P; 260/251 R; 260/453 RW
[51] Int. Cl.² ...................... C07F 9/65; A01N 9/36
[58] Field of Search ................. 260/251 P; 424/200

[56] References Cited
UNITED STATES PATENTS

| | | | |
|---|---|---|---|
| 2,754,243 | 7/1956 | Gysin et al. | 260/251 P X |
| 3,862,188 | 1/1975 | Milzner et al. | 260/251 P |

*Primary Examiner*—Donald G. Daus
*Assistant Examiner*—Diana G. Rivers
*Attorney, Agent, or Firm*—Karl F. Jorda

[57] ABSTRACT

Pyrimidyl-thio and dithio-phosphoric acid esters of the formula

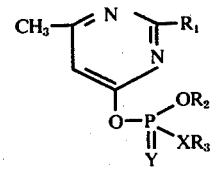

wherein
$R_1$ represents a $C_3$ to $C_6$ cycloalkyl group,
$R_2$ and $R_3$ each represent a $C_1$ to $C_5$ alkyl group and
X and Y each represent oxygen or sulfur, processes for their manufacture, and their use in pest control.

12 Claims, No Drawings

PYRIMIDYL THIO- AND DITHIO-PHOSPHORIC ACID ESTERS

DETAILED DISCLOSURE

The present invention relates to pyrimidyl-thio and dithio-phosphoric acid esters, to processes for their preparation and to their use in pest control. The pyrimidyl-thio and dithio-phosphoric acid esters have the formula

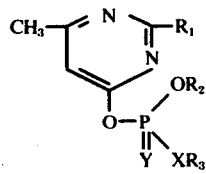

wherein
$R_1$ represents a $C_3$ to $C_8$ cycloalkyl group,
$R_2$ and $R_3$ each represent a $C_1$ to $C_5$ alkyl group and
X and Y each represent oxygen or sulfur.

Examples of cycloalkyl groups which are possible for $R_1$ include: cyclopropyl, cyclopentyl and cyclohexyl.

The alkyl group which are possible for $R_2$ and $R_3$ can be straight-chained or branched. Examples of such groups include: methyl, ethyl, n-propyl, isopropyl, n-butyl, secondary and tertiary butyl, n-pentyl and isomers thereof.

Preferred compounds on account of their action are those of the formula I, wherein
$R_1$ represents cyclopropyl, cyclopentyl or cyclohexyl,
$R_2$ represents methyl or ethyl,
$R_3$ represents methyl, ethyl, n-propyl, iso-propyl or n-pentyl,
X represents oxygen or sulfur and
Y represents sulphur.

Particularly preferred compounds, however, are those of the formula I, wherein
$R_1$ represents cyclopropyl,
$R_2$ represents ethyl,
$R_3$ represents ethyl or n-propyl,
X represents oxygen or sulfur and
Y represents sulfur.

The compounds of the formula I can be manufactured by the following methods which are known per se:

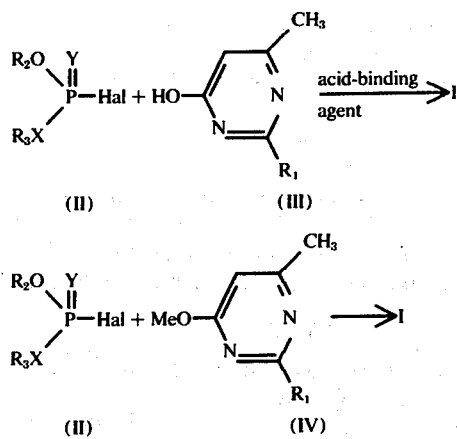

In the formulae II to IV, the symbols $R_1$, $R_2$, $R_3$, X and Y have the same meanings given for the formula I and Hal represents a halogen atom, in particular, chlorine or bromine, and Me represents an alkali metal, in particular sodium or potassium. Suitable acid-binding agents are tertiary amines, e.g., trialkylamines, pyridine or dialkylamines, inorganic bases such as hydrides, hydroxides, carbonates or bicarbonates of alkali metals and alkali-earth metals.

The processes are carried out at normal pressure, at a temperature between 0° to 150° C, preferably between 20° to 80° C, and in solvents or diluents which are inert towards the reactants. Examples of suitable solvents and diluents are: aromatic hydrocarbons, e.g., benzene, toluene; halogenated hydrocarbons, e.g., chlorobenzene, polychlorobenzenes, bromobenzenes, chlorinated alkenes with 1 to 3 carbon atoms; ethers, e.g., dioxan, tetrahydrofuran; esters, e.g., ethyl acetate; ketones, e.g., acetone, methyl-ethyl ketone, diethyl ketone; nitriles, e.g., acetonitrile, etc.

The starting materials of formulae II, III and IV can be prepared by methods analogous to known methods, e.g., analogous to those described in "Organic Reactions II," pp. 1 to 48.

Compounds of formula I have a broad biocidal action, and are therefore suitable for the control of diverse plant and animal pests. Compared with analogous compounds from the U.S. Pat. No. 2,754,243, compounds of formula I have a surprisingly better activity against, e.g., *Leptinotarsa decemlineata* and *Heliothis virescens*.

The said compounds are suitable for the control of all development stages, such as, e.g., eggs, larvae, pupae, nymphs and adults of insects of the families: Acrididae, Blattidae, Gryllidae, Gryllotalpidae, Tettigonidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Tineidae, Noctuidae, Lymantriidae, Pyralidae, Galleridae, Culicidae, Tipulidae, Stomoxydae, Muscidae, Calliphoridae, Trypediadae and Pulicidae, as well as acarids of the families: Ixodidae, Argasidae, Tetranychidae and Dermanyssidae.

The insecticidal or acaricidal action can be appreciably broadened and adapted to suit given circumstances by the addition of other insecticides and/or acaricides. Suitable additives are, for example: organic phosphorous compounds, nitrophenols and derivatives thereof, formamidines, carbamates, chlorinated hydrocarbons and pyrethroids.

The compounds of formula I can be used as such or together with suitable carriers and/or additives. Suitable carriers and additives may be in solid or liquid form, and are substances commonly used in formulation practice, such as, e.g., natural or regenerated substances, solvents, dispersing agents, wetting agents, adhesives, thickeners, binders and/or fertilizers. For application, the compounds of formula I can be formulated as dusts, emulsion concentrates, granulates, dispersions, sprays or solutions. Also to be mentioned are cattle dips and spray races, in which aqueous preparations are used.

The agents according to the present invention are prepared in a manner known per se by the intimate mixing and/or grinding of active substances of formula I with suitable carries, optionally with the addition of dispersing agents or solvents which are inert to the active substances. The active substances can be obtained and used in the following forms:

Solid Preparations:
 dusts, scattering agents, granulates, coated granulates, impregnated granulates and homogeneous granulates;

Liquid Preparations:
 a. water - dispersible active - substance concentrate: wettable powders, pastes or concentrations;
 b. solutions.

The content of active substance in the described agents is between 0.1 and 95%; it is to be mentioned in this respect, however, that concentrations of up to 99.5% can be used where the said agents are applied from an airplane or by means of other suitable application devices. The active substances of formula I can be formulated, for example, as follows:

DUSTS

The following substances are used in the preparation of: (a) a 5% dust and, (b) a 2% dust:

a.
 5 parts of active substance,
 95 parts of talcum.

b.
 2 parts of active substance,
 1 part of highly dispersed silicic acid,
 97 parts of talcum.

The active substances are mixed and ground with the carriers.

Granulate

The following substances are used to prepare a 5% granulate:
 5 parts of active substance,
 0.25 part of epichlorohydrin,
 0.25 part of cetyl polyglycol ether,
 3.50 parts of polyethylene glycol,
 91 parts of kaolin.

The active substance is mixed with epichlorhydrin and dissolved with 6 parts of acetone; the polyethylene glycol and cetyl polyglycol ether are then added. The solution thus obtained is sprayed onto kaolin, and the acetone subsequently evaporated off in vacuo.

Wettable Powders

The following constituents are used for the preparation of: (a) a 40%, (b) and (c) a 25% and, (d) a 10% wettable powders:

a.
 40 parts of active substance,
 5 parts of sodium lignin sulphonate,
 1 part of sodium dibutyl-naphthalene-sulphonate,
 54 parts of silicic acid;

b.
 25 parts of active substance;
 4.5 parts of calcium lignin sulphonate,
 1.9 parts of champagne chalk/hydroxy-ethyl cellulose mixture (1:1)
 1.5 parts of sodium dibutyl naphthalene sulphonate,
 19.5 parts of silicic acid,
 19.5 parts of champagne chalk,
 28.1 parts of kaolin;

c.
 25 parts of active substance,
 2.5 parts of isooctylphenoxy-polyoxyethylene-ethanol,
 1.7 parts of champagne chalk/hydroxyethyl cellulose mixture (1:1)
 8.3 parts of sodium aluminium silicate,
 16.5 parts of kieselguhr
 46 parts of kaolin;

d.
 10 parts of active substance,
 3 parts of a mixture of the sodium salts of saturated fatty alcohol sulphates,
 5 parts of naphthalenesulphonic acid/formaldehyde condensate
 82 parts of kaolin.

The active substance is intimately mixed in suitable mixers, with the additives, the mixture being then ground in the appropriate mills and rollers. Wettable powders are obtained which can be diluted with water to give suspensions of any desired concentration.

Emulsifiable Concentrates

The following substances are used to prepare: (a) a 10% and, (b) a 25% emulsifiable concentrate:

a.
 10 parts of active substance
 3.4 parts of epoxidized vegetable oil,
 3.4 parts of a combination emulsifier consisting of fatty alcohol polyglycol ethers and alkyl arylsulphonate calcium salt,
 40 parts of dimethylformamide,
 43.2 parts of xylene;

b.
 25 parts of active substance
 2.5 parts of epoxidized vegetable oil,
 10 parts of an alkylarylsulphunate/fatty alcohol polyglycol ethers mixture,
 5 parts of dimethylformamide,
 57.5 parts of xylene.

From these concentrates it is possible to prepare, by dilution with water, emulsions of any desired concentration.

Spray

The following constituents are used to prepare: (a) a 5% and, (b) a 95% spray:

a.
 5 parts of active substance,
 1 part of epichlorhydrin,
 94 parts of ligrion (boiling limits 150–190° C)

b.
 95 parts of active substance,
 5 parts of epichlorhydrin.

The following examples show a process and insecticidal and acaricidal tests. They are included here for illustrative purposes only and are not intended as limitations. Temperatures are given in degrees centigrade.

EXAMPLE 1

Synthesis of 0,0-Diethyl-0-[2-cyclopropyl-4-methyl-pyrimidyl(6)]-thiophosphate a. Preparation of the Intermediate Cyclopropylmethylether Hydrochloride

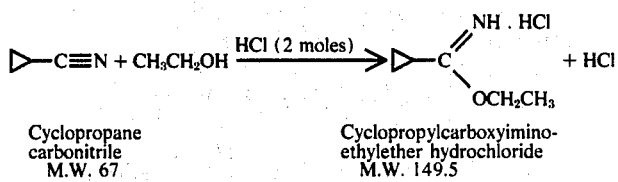

| Cyclopropane | Cyclopropylcarboxyimino- |
| carbonitrile | ethylether hydrochloride |
| M.W. 67 | M.W. 149.5 |

Into a 1-liter 3-neck flask equipped with agitator, thermometer, subsurface gas inlet tube, water-cooled condenser, and exit gas bubbler containing 50% NaOH is charged 268 g of cyclopropylcarbonitrile 100% (4.0 moles) and 195 g of anhydrous ethanol SD 2B (4.22 moles, an 9% excess over theory). The mixture is agitated and about 292 g hydrogen chloride 100% (8 moles) is bubbled under the surface over a 4 hour period at 20°–25° with ice bath cooling (Brooks Flowmeter R-2-15-A with sapphire float at 111 mm gives a gain in weight of ca. 292g in 4 hours). Following the HCl addition, the gain in weight is determined and the reaction mixture is agitated 2 hours longer at 20°–25°. The colorless solution of product may be stored in the refrigerator without deterioration. The produce is analyzed by anhdyrous titration to determine free HCl and assay as iminoether hydrochloride. Infrared analysis shows cyclopropylcarbonitrile and ethyl cyclopropylcarboxylate, if present. Generally, a yield of greater than 99% is obtained in the laboratory.

b. Preparation of the Intermediate Cyclopropylcarboxylic Acid Amidine Hydrochloride charge is derived from 2.5 moles cyclopropylcarbonitrile. The exothermic reaction is controlled at 20°–25° by regulating the rate of iminoether drop while cooling with an ice bath. It is desirable to add the first portion of the iminoether rapidly (over about a fifteen minute period) at a maxium temperature of 25° until the pH meter drops to 9.6 and the indicator paper (pHydrion range 8–9.5) reads 9.0. The remaining iminoether is added over a half-hour period, along with approximately 100 g (2.5 moles) of sodium hydroxide 100% (200 g 50% NaOH) at a temperature of 25° + 3° and a pH of 8.9–9.2 by paper (9.5–9.8 by meter). Following completion of the iminoether and caustic drop, the reaction mixture containing a suspension of sodium chloride is stirred for 1 hour at 25°. It is to be emphasized that at least a full hour's "aging" time is desirable to insure maximum amidine yield. The product, cyclopropylcarboxylic acid amidine hydrochloride is present as an aqueous solution, volume ca. 1015 ml (ca. 1150 g). At pH 9 it is quite stable at refrigerator temperature and may be stored overnight with no appreciable yield loss. The yield as determined by assay is 95–98%.

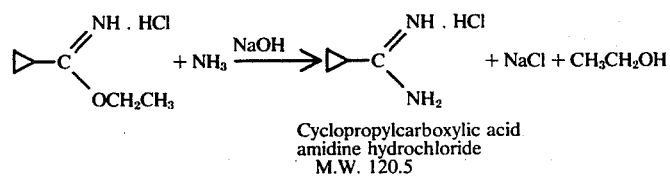

Cyclopropylcarboxylic acid
amidine hydrochloride
M.W. 120.5

Into a 2-liter 3-neck flask equipped with blade stirrer, thermometer, Jena-Sargent combination glass electrode (S-30070-15) and Bechman expanded scale pH c. Preparation of Intermediate 2-Cyclopropyl-4-methyl-6-hydroxypyrimidine ("Oxypyrimidine"Ring Closure and Neutralization)

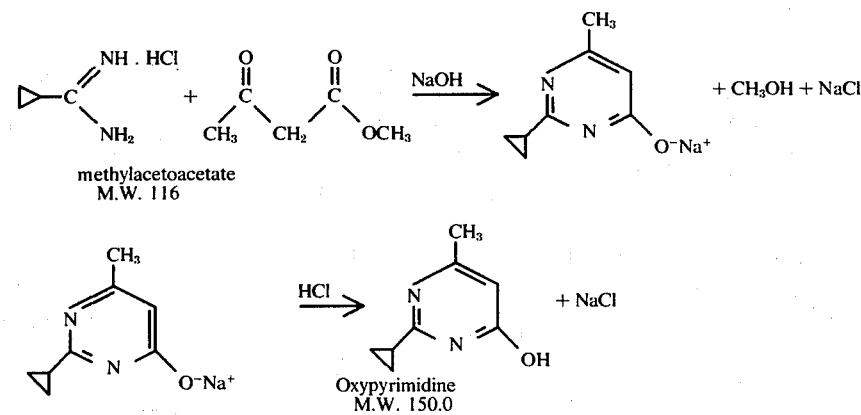

methylacetoacetate
M.W. 116

Oxypyrimidine
M.W. 150.0 meter are charged 51.0 g of ammonia 100% (182 g ammonia 28–30%), a 20% excess over theory or a total of 3.0 moles, and 240 g water as a diluent. The water-ammonia mixture is cooled to ca. 10° with an ice bath, whereupon 379 g cyclopropylmethyliminoethylether hydrochloride 100% (M.W. 149.5) or approximately 474 gms at 79% assay is started in as a thin stream. This 283 g of cyclopropylcarboxylic acid amidine hydrochloride 100% (M.W. 120.5, 2.35 moles) from one charge of 2.5 moles of cyclopropylcarbonitrile or about 1150 g solution are cooled to 0.5° in a 2-liter flask equipped with stirrer, thermometer, two dropping funnels and Jena-Sargent combination pH electrode (Model No. S-30070-15). Immediately upon cooling with a dry ice acetone bath 377 g of methyl acetoacetate 100% (M.W. 116) or 1.30 moles per mole of cyclopropylcarbonitrile is added to the slurry with agitation. (pH decreases to 8.5 on 8.0–9.5 pHydrion paper). After stirring to insure proper mixing 140 g sodium hydroxide 50% is added over a 5 minute period, thereby gradually increasing the pH to 12.3–12.6 by the use of 11.5–13.5 pHydrion paper. (Strong orange coloration of Mimosa paper.) During the addition the temperature rises to approximately 40°–45° despite full cooling. The pH (as read by meter) drops back to 11.5. Not all the caustic is fed during the initial addition but the remainder is added over the next 15–30 minute period to maintain the 12.3–12.6 pH level. The reaction is stirred for at least one additional hour at 35°–40°. Then it is transferred to a 3-liter 3-neck flask along with 600 g of water prior to neutralization.

For precipitation of the oxypyrimidine about 93 g of hydrochloric acid 100% (253 g 37–38 HCl) is added with stirring and cooling over a 15–25 minute period until a pH of 6 is reached on the meter. Very fast agitation is needed to effect mixing. Following the neutralization, the cooling is continued until a temperature of 8°–10° is reached. The mixture is filtered as rapidly as possible at maximum temperature of 10°. The neutralized reaction mass is washed with cold filtrate. No aqueous wash is used to rinse the flask to minimize solubility loss. The filter cake should be kept under vacuum on the filter for at least two hours to remove as much filtrate as possible before drying. The oxypyrimidine is dried at 60° for 24 hours under vacuum in the oven. A yield of 337.5 g of oxypryrimidine 100%, 90% of theory is obtained. (Structure confirmation was made by NMR.)

d. Condensation to Desired Product

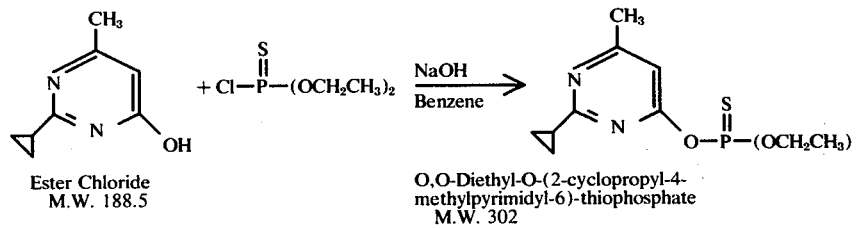

Ester Chloride
M.W. 188.5

O,O-Diethyl-O-(2-cyclopropyl-4-methylpyrimidyl-6)-thiophosphate
M.W. 302

Into a 3-liter, 5-neck, baffled flask equipped with thermometer, blade stirrer, electric heating mantle, Barret distillate receiver and condenser, is charged 550 g of benzene and 315 g of oxypyrimidine 100% (2.1 moles, 5% excess over theory) and heated to reflux (85°). After all water has been azeotroped from the slurry the following additions are made simultaneously. 377 g of diethyl thiophosphoric acid chloride (ester chloride) (2.0 moles) continuously over a 2-hour period and 176 g 50% NaOH (2.2 moles, 10% excess over theory) continuously over 2 ¼ hours. The temperature drops to 83°–85° at the start of the additions and rises to 93°–95° at completion of the additions. The azeotroped water is collected in the receiver and the solvent is returned to the reactor. The batch is maintained at reflux until the ester chloride level is reduced to less than 0.25% by glc analysis (5–6 hours from start of ester chloride and NaOH additions). After the reaction is completed the reaction mass is cooled to 60°–70° and washed as follows: 400 g of $H_2O$ and 10–30 g of 50% NaOH are added to pH 12.5 in the aqueous phase, agitated for 15 minutes and the water layer (bottom layer) is removed. 400 g of $H_2O$ and 1–5 g $H_3SO_4$ are added to pH 1–2 in the aqueous phase, agitated for 15 minutes, and the water layer (bottom layer) is removed. 400 g of $H_2O$ and 2 g $Na_2CO_3$ are added to pH 7–8 in the aqueous phase, agitated for 15 minutes at 50°–60°, allowed to settle 30–60 minutes, and the water layer (bottom layer) is removed. The remaining product layer is stripped at 100° on the roto-vap at 25 in. Hg vacuum. A yield of 94–95% based on ester chloride charged is obtained (yield calculated using GLC assay).

e. Variation of the Final Step 138 parts of potassium carbonate and 2000 parts of benzene are added to 150 parts of 2-cyclopropyl-4-methyl-6-hydroxy-pyrimidine and the whole is heated to boiling while stirring. During this process the water liberated on the formation of the potassium enolate is azeotropically distilled off with benzene. As soon as no more water is formed in the distillate, the mixture is cooled to 60°–70°, 190 parts of diethyl thiophosphoric acid chloride are added dropwise and finally the whole is boiled under reflux for 10 hours. After cooling, potassium carbonate solution is added to the reaction mixture while stirring well while the aqueous layers colours phenolphthalein paper red. On removal of the aqueous layers, the solvent is distilled off. 0,0-diethyl-0-[2-cyclopropyl-4-methyl-pyrimidyl (6)]-thiophosphate remains which is suitable without any further purification as active ingredient for insecticidal and acaricidal preparations.

The following compounds can be made in an analogous

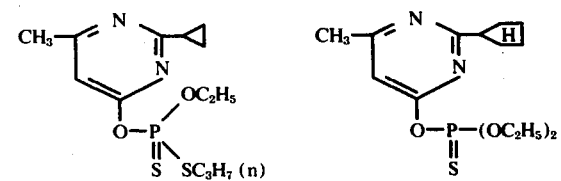

EXAMPLE 2

Insecticidal Stomach Poison Action

Cotton and potato plants were sprayed with a 0.05% aqueous active substance emulsion (obtained from a 10% emulsifiable concentrate).

After the drying of the obtained coating *spodoptera littoralis* or *heliothis verescens* larvae ($L_3$-stage) were placed on the cotton plants, and Colorado beetle larvae (*Leptinotarsa decemlineata*) on the potato plants. The tests were carried out at 25° with 60% relative humidity.

Compounds according to Example 1 exhibited in the above tests a good insecticidal stomach poison action against *Spodoptera littoralis*, *Heliothis virescens* and *Leptinotarsa decemlineata* larvae.

EXAMPLE 3

Acaricidal Action

*Phaseolus vulgaris* (plants) were infested, 12 hours before the test for acaricidal action, with an infested piece of leaf from a mass culture of *Tetranychus urticae*.

The transferred mobile stages were sprayed with the emulsified test preparations from a chromatography - sprayer in manner causing no overflowing of the spray liquor.

An assessment was made after 2 and 7 days by examination under a binocular of living larvae and dead larvae, adults and eggs.

The treated plants were kept during the "holding time" in greenhouse compartments at 25°.

Compounds according to Example 1 were effective in the above test against adults, larvae and eggs and *Tetranychus urticae*.

Example 4

Action against *Chilo suppressalis*

Six rice plants at a time of the variety Caloro were transplanted into plastic pots (diameter at the top = 17 cm) and reared to a height of about 60 cm. Infestation with *chilo suppressalis* larvae ($L_1$: 3–4 mm long) took place 2 days after the active substance had been applied in granule form to the paddy water (rate of application : 8 kg of active substance per hectare). Evaluation of the insecticidal action took place 10 days after application of the granules.

Compounds according to Example 1 were active in the above test against *Chilo suppressalis*.

What is claimed is:

1. A compound of the formula

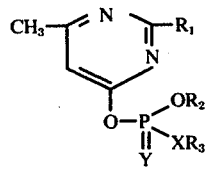

wherein
$R_1$ represents a $C_3$ to $C_6$ cycloalkyl group,
$R_2$ and $R_3$ each represents a $C_1$ to $C_5$ alkyl group, and
X and Y each represent oxygen or sulfur.

2. A compound according to claim 1, wherein $R_1$ represents cyclopropyl, cyclopentyl or cyclohexyl, $R_2$ represents methyl or ethyl, $R_3$ represents methyl, ethyl, n-propyl, isopropyl or n-pentyl, X represents oxygen or sulfur and Y represents sulfur.

3. A compound according to claim 2, wherein $R_1$ represents cyclopropyl, $R_2$ represents ethyl, $R_3$ represents ethyl or n-propyl, X represents oxygen or sulfur and Y represents sulfur.

4. The compound according to claim 3 of the formula

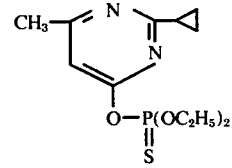

5. A pesticidal composition for combating pests selected from the group consisting of insects and acarids comprising a pesticidally effective amount of a compound according to claim 1 and a carrier.

6. A pesticidal composition for combating pests selected from the group consisting of insects and acarids comprising a pesticidally effective amount of a compound according to claim 2 and a carrier.

7. A pesticidal composition for combating pests selected from the group consisting of insects and acarids comprising a pesticidally effective amount of a compound according to claim 3 and a carrier.

8. A pesticidal composition for combating pests selected from the group consisting of insects and acarids comprising a pesticidally effective amount of a compound according to claim 4 and a carrier.

9. A method of combating pests selected from the group consisting of insects and acarids which comprises applying thereto a psticidally effective amount of a compound according to claim 1.

10. A method of combating pests selected from the group consisting of insects and acarids which comprises applying thereto a pesticidally effective amount of a compound according to claim 2.

11. A method of combating pests selected from the group consisting of insects and acarids which comprises applying thereto a pesticidally effective amount of a compound according to claim 3.

12. A method of combating pests selected from the group consisting of insects and acarids which comprises applying thereto a pesticidally effective amount of a compound according to claim 4.

* * * * *